US008557179B2

(12) United States Patent
Larsen et al.

(10) Patent No.: US 8,557,179 B2
(45) Date of Patent: Oct. 15, 2013

(54) NON-POROUS MATERIAL AS STERILIZATION BARRIER

(75) Inventors: Bjørn Gullak Larsen, Birkerød (DK); Brian Jensen, Brønshøj (DK); Ulla Holm Christensen, Sæby (DK)

(73) Assignee: Novo Nordisk A/S, Bagsvaerd (DK)

( * ) Notice: Subject to any disclaimer, the term of this patent is extended or adjusted under 35 U.S.C. 154(b) by 545 days.

(21) Appl. No.: 12/740,765

(22) PCT Filed: Oct. 31, 2008

(86) PCT No.: PCT/EP2008/064762
§ 371 (c)(1),
(2), (4) Date: Sep. 8, 2010

(87) PCT Pub. No.: WO2009/056616
PCT Pub. Date: May 7, 2009

(65) Prior Publication Data
US 2011/0008206 A1 Jan. 13, 2011

Related U.S. Application Data

(60) Provisional application No. 60/985,301, filed on Nov. 5, 2007.

(30) Foreign Application Priority Data

Oct. 31, 2007 (EP) .................................... 07119760

(51) Int. Cl.
*A61L 2/08* (2006.01)
*A61L 2/20* (2006.01)

(52) U.S. Cl.
USPC .............................................. 422/26; 422/33

(58) Field of Classification Search
USPC ...................................................... 422/26, 33
See application file for complete search history.

(56) References Cited

U.S. PATENT DOCUMENTS

| 2,605,765 A | 8/1952 | Kollsman |
| 2,960,097 A | 11/1960 | Scheffler |
| 2,980,032 A | 4/1961 | Schneider |

(Continued)

FOREIGN PATENT DOCUMENTS

| CA | 2239457 | 12/1999 |
| CN | 1612758 | 5/2005 |

(Continued)

OTHER PUBLICATIONS

International Search Report mailed Jul. 5, 2007 in international application No. PCT/EP2007/053923.

(Continued)

*Primary Examiner* — Kevin Joyner
(74) *Attorney, Agent, or Firm* — Wesley A. Nicolas; Marc A. Began; Reza Green

(57) ABSTRACT

The invention provides a device comprising a sealed interior portion with at least one opening covered by a sterilization barrier formed from a non-porous material allowing a sterilization gas to penetrate but prevents germs from penetrating. The size and configuration of the at least one sterilization barrier formed from a non-porous material are adapted to allow at least 50% of the sterilization gas, that would pass between a sterilization gas-containing exterior and the sealed interior portion when a pressure difference is created there between, to pass through the non-porous material.

3 Claims, 7 Drawing Sheets

(56) References Cited

U.S. PATENT DOCUMENTS

| | | |
|---|---|---|
| 3,705,601 A | 12/1972 | Arisland |
| 4,016,879 A | 4/1977 | Mellor |
| 4,077,405 A | 3/1978 | Haerten et al. |
| 4,137,020 A | 1/1979 | Ito et al. |
| 4,245,634 A | 1/1981 | Albisser et al. |
| 4,262,824 A | 4/1981 | Hrynewycz |
| 4,340,048 A | 7/1982 | Eckenhoff |
| 4,370,305 A | 1/1983 | Affonso |
| 4,378,015 A | 3/1983 | Wardlaw |
| 4,399,824 A | 8/1983 | Davidson |
| 4,402,407 A | 9/1983 | Maly |
| 4,519,792 A | 5/1985 | Dawe |
| 4,529,401 A | 7/1985 | Leslie et al. |
| 4,544,369 A | 10/1985 | Skakoon et al. |
| 4,552,561 A | 11/1985 | Eckenhoff et al. |
| 4,645,491 A | 2/1987 | Evans |
| 4,657,490 A | 4/1987 | Abbott |
| 4,710,170 A | 12/1987 | Haber et al. |
| 4,734,092 A | 3/1988 | Millerd |
| 4,753,651 A | 6/1988 | Eckenhoff |
| 4,755,173 A | 7/1988 | Konopka et al. |
| 4,788,556 A | 11/1988 | Hoisington et al. |
| 4,871,351 A | 10/1989 | Feingold |
| 4,877,034 A | 10/1989 | Atkins et al. |
| 4,886,499 A | 12/1989 | Cirelli et al. |
| 4,894,054 A | 1/1990 | Miskinyar |
| 4,928,528 A | 5/1990 | Marques |
| 4,994,078 A | 2/1991 | Jarvik |
| 5,008,110 A | 4/1991 | Benecke et al. |
| 5,049,146 A | 9/1991 | Bringham et al. |
| 5,076,890 A | 12/1991 | Balembois |
| 5,122,116 A | 6/1992 | Kriesel et al. |
| 5,122,201 A | 6/1992 | Frazier et al. |
| 5,149,340 A | 9/1992 | Waycuilis |
| 5,169,390 A | 12/1992 | Athayde et al. |
| 5,211,201 A | 5/1993 | Kamen et al. |
| 5,224,843 A | 7/1993 | van Lintel |
| 5,256,157 A | 10/1993 | Samiotes et al. |
| 5,336,052 A | 8/1994 | Zöllner et al. |
| 5,390,671 A | 2/1995 | Lord et al. |
| 5,391,950 A | 2/1995 | Krawczak |
| 5,482,473 A | 1/1996 | Lord et al. |
| 5,485,917 A | 1/1996 | Early |
| 5,494,415 A | 2/1996 | Morita |
| 5,514,095 A | 5/1996 | Brightbill |
| 5,527,287 A | 6/1996 | Miskinyar |
| 5,527,288 A | 6/1996 | Gross et al. |
| 5,568,806 A | 10/1996 | Cheney, II et al. |
| 5,584,808 A | 12/1996 | Healy |
| 5,584,813 A | 12/1996 | Livingston et al. |
| 5,586,085 A | 12/1996 | Lichte |
| 5,609,572 A | 3/1997 | Lang |
| 5,647,853 A | 7/1997 | Feldmann et al. |
| 5,720,391 A | 2/1998 | Dohm et al. |
| 5,776,109 A | 7/1998 | Urrutia |
| 5,814,020 A | 9/1998 | Gross |
| 5,851,197 A | 12/1998 | Marano et al. |
| 5,858,001 A | 1/1999 | Tsals et al. |
| 5,860,952 A | 1/1999 | Quinn |
| 5,913,856 A | 6/1999 | Chia et al. |
| 5,925,017 A | 7/1999 | Kriesel et al. |
| 5,928,194 A | 7/1999 | Maget |
| 5,931,814 A | 8/1999 | Alex et al. |
| 5,941,611 A | 8/1999 | Trzmiel et al. |
| 5,954,643 A | 9/1999 | VanAntwerp et al. |
| 5,957,895 A | 9/1999 | Sage et al. |
| 5,968,011 A | 10/1999 | Larsen et al. |
| 5,997,501 A | 12/1999 | Gross et al. |
| 6,045,534 A | 4/2000 | Jacobsen et al. |
| 6,060,319 A | 5/2000 | Deetz et al. |
| 6,074,369 A | 6/2000 | Sage et al. |
| 6,083,196 A | 7/2000 | Trautman et al. |
| 6,088,619 A | 7/2000 | Hein et al. |
| 6,099,512 A | 8/2000 | Urrutia |
| 6,120,492 A | 9/2000 | Finch et al. |
| 6,123,519 A | 9/2000 | Kato et al. |
| 6,126,637 A | 10/2000 | Kriesel et al. |
| 6,132,755 A | 10/2000 | Eicher et al. |
| 6,165,155 A | 12/2000 | Jacobsen et al. |
| 6,241,704 B1 | 6/2001 | Peterson et al. |
| 6,270,478 B1 | 8/2001 | Mernøe |
| 6,280,148 B1 | 8/2001 | Zengerle et al. |
| 6,293,925 B1 | 9/2001 | Safabash et al. |
| 6,302,866 B1 | 10/2001 | Marggi |
| 6,302,869 B1 | 10/2001 | Klitgaard |
| 6,358,731 B1 | 3/2002 | Hsu |
| 6,364,865 B1 | 4/2002 | Lavi et al. |
| 6,485,461 B1 | 11/2002 | Mason et al. |
| 6,500,150 B1 | 12/2002 | Gross et al. |
| 6,551,276 B1 | 4/2003 | Mann et al. |
| 6,554,791 B1 | 4/2003 | Cartledge et al. |
| 6,555,986 B2 | 4/2003 | Moberg |
| 6,558,351 B1 | 5/2003 | Steil et al. |
| 6,589,229 B1 | 7/2003 | Connelly et al. |
| 6,613,015 B2 | 9/2003 | Sandstrom et al. |
| 6,622,037 B2 | 9/2003 | Kasano |
| 6,656,159 B2 | 12/2003 | Flaherty |
| 6,716,192 B1 | 4/2004 | Orosz |
| 6,740,059 B2 | 5/2004 | Flaherty |
| 6,749,587 B2 | 6/2004 | Flaherty |
| 6,808,691 B1 | 10/2004 | Herve et al. |
| 6,818,178 B2 | 11/2004 | Koh et al. |
| 6,878,136 B2 | 4/2005 | Fleury et al. |
| 6,949,084 B2 | 9/2005 | Marggi et al. |
| 6,960,192 B1 | 11/2005 | Flaherty et al. |
| 7,052,483 B2 | 5/2006 | Wojcik |
| 7,070,580 B2 | 7/2006 | Nielsen |
| 7,097,631 B2 | 8/2006 | Trautman et al. |
| 7,097,690 B2 | 8/2006 | Usher et al. |
| 7,141,023 B2 | 11/2006 | Diermann et al. |
| 7,144,384 B2 | 12/2006 | Gorman et al. |
| 7,303,073 B2 | 12/2007 | Raynal-Olive et al. |
| 7,744,570 B2 | 6/2010 | Fangrow |
| 2001/0025168 A1 | 9/2001 | Gross et al. |
| 2002/0040083 A1 | 4/2002 | Kuwaki et al. |
| 2002/0040208 A1 | 4/2002 | Flaherty et al. |
| 2002/0055711 A1 | 5/2002 | Lavi et al. |
| 2002/0064468 A1 | 5/2002 | Wade |
| 2002/0123740 A1 | 9/2002 | Flaherty et al. |
| 2002/0161332 A1 | 10/2002 | Ramey |
| 2002/0169416 A1 | 11/2002 | Gonnelli et al. |
| 2003/0009131 A1 | 1/2003 | Van Antwerp et al. |
| 2003/0009133 A1 | 1/2003 | Ramey |
| 2003/0029501 A1 | 2/2003 | Williamson et al. |
| 2003/0060781 A1 | 3/2003 | Mogensen et al. |
| 2003/0065308 A1 | 4/2003 | Lebel et al. |
| 2003/0069546 A1 | 4/2003 | Sandstrom et al. |
| 2003/0072013 A1* | 4/2003 | Lin et al. .................. 422/292 |
| 2003/0073952 A1 | 4/2003 | Flaherty et al. |
| 2003/0088238 A1 | 5/2003 | Poulsen et al. |
| 2003/0114797 A1 | 6/2003 | Vaillancourt et al. |
| 2003/0135159 A1 | 7/2003 | Daily et al. |
| 2003/0167035 A1 | 9/2003 | Flaherty et al. |
| 2003/0187395 A1 | 10/2003 | Gabel et al. |
| 2003/0194328 A1 | 10/2003 | Bryant et al. |
| 2003/0199823 A1 | 10/2003 | Bobroff et al. |
| 2003/0216686 A1 | 11/2003 | Lynch et al. |
| 2003/0236498 A1 | 12/2003 | Gross et al. |
| 2004/0051674 A1 | 3/2004 | Mahringer |
| 2004/0087240 A1 | 5/2004 | Chen et al. |
| 2004/0098068 A1 | 5/2004 | Carbunaru et al. |
| 2004/0115068 A1 | 6/2004 | Hansen et al. |
| 2004/0116905 A1 | 6/2004 | Pedersen et al. |
| 2004/0127844 A1 | 7/2004 | Flaherty |
| 2004/0158207 A1 | 8/2004 | Hunn et al. |
| 2004/0162521 A1 | 8/2004 | Bengtsson |
| 2004/0171403 A1 | 9/2004 | Mikkola |
| 2004/0199123 A1 | 10/2004 | Nielsen |
| 2004/0204673 A1 | 10/2004 | Flaherty et al. |
| 2004/0220497 A1 | 11/2004 | Findlay et al. |
| 2004/0220536 A1 | 11/2004 | VanTassel et al. |
| 2004/0260233 A1 | 12/2004 | Garibotto et al. |
| 2005/0006309 A1 | 1/2005 | Effenhauser et al. |
| 2005/0022274 A1 | 1/2005 | Campbell et al. |

(56) References Cited

U.S. PATENT DOCUMENTS

| | | |
|---|---|---|
| 2005/0077225 A1 | 4/2005 | Usher et al. |
| 2005/0101933 A1 | 5/2005 | Marrs et al. |
| 2005/0171513 A1 | 8/2005 | Mann et al. |
| 2005/0203461 A1 | 9/2005 | Flaherty et al. |
| 2005/0240154 A1 | 10/2005 | Mogensen et al. |
| 2006/0015063 A1 | 1/2006 | Butikofer et al. |
| 2006/0017576 A1 | 1/2006 | Gordon et al. |
| 2006/0020300 A1 | 1/2006 | Nghiem et al. |
| 2006/0142698 A1 | 6/2006 | Ethelfeld |
| 2006/0200073 A1 | 9/2006 | Radmer et al. |
| 2006/0264835 A1 | 11/2006 | Nielsen et al. |
| 2007/0021733 A1 | 1/2007 | Hansen et al. |
| 2007/0073228 A1 | 3/2007 | Mernoe et al. |
| 2007/0104596 A1 | 5/2007 | Preuthun et al. |
| 2007/0112301 A1 | 5/2007 | Preuthun et al. |
| 2008/0009805 A1 | 1/2008 | Ethelfeld |
| 2008/0023346 A1* | 1/2008 | Vonderwalde ............... 206/210 |
| 2009/0163874 A1 | 6/2009 | Krag et al. |

FOREIGN PATENT DOCUMENTS

| | | |
|---|---|---|
| DE | 2552446 | 5/1977 |
| DE | 10255817 | 6/2004 |
| DK | PA 2003 00696 | 5/2003 |
| DK | PA 2003 00697 | 5/2003 |
| EP | 398583 | 11/1990 |
| EP | 568176 | 11/1993 |
| EP | 937475 | 8/1999 |
| EP | 1177802 | 2/2002 |
| EP | 1256356 | 11/2002 |
| EP | 1329233 | 7/2003 |
| EP | 1475113 | 11/2004 |
| EP | 1527792 | 5/2005 |
| GB | 2020735 | 11/1979 |
| GB | 2212387 | 7/1989 |
| JP | 2000-104659 | 4/2000 |
| JP | 2000-513259 | 10/2000 |
| JP | 2000-515394 | 11/2000 |
| JP | 2002-505601 | 2/2002 |
| WO | WO 90/07942 | 7/1990 |
| WO | WO 96/07397 | 3/1996 |
| WO | WO 96/30679 | 10/1996 |
| WO | WO 97/21457 | 6/1997 |
| WO | WO 98/57683 | 12/1998 |
| WO | WO 99/62576 | 12/1999 |
| WO | WO 02/02165 | 1/2002 |
| WO | WO 02/04048 | 1/2002 |
| WO | WO 02/05889 | 1/2002 |
| WO | WO 02/15889 | 2/2002 |
| WO | WO 02/15965 | 2/2002 |
| WO | WO 02/40083 | 5/2002 |
| WO | WO 02/45574 | 6/2002 |
| WO | WO 02/47746 | 6/2002 |
| WO | WO 02/055132 | 7/2002 |
| WO | WO02/070024 | 9/2002 |
| WO | WO 02/081012 | 10/2002 |
| WO | WO 02/100457 | 12/2002 |
| WO | WO 03/026726 | 4/2003 |
| WO | WO 03/026728 | 4/2003 |
| WO | WO 03/080169 | 10/2003 |
| WO | WO 03/089028 | 10/2003 |
| WO | WO 03/090509 | 11/2003 |
| WO | WO 03/099358 | 12/2003 |
| WO | WO 2004/009160 | 1/2004 |
| WO | WO 2004/029457 | 4/2004 |
| WO | WO 2004/030728 | 4/2004 |
| WO | WO 2004/098682 | 11/2004 |
| WO | WO 2004/098683 | 11/2004 |
| WO | WO 2004/098684 | 11/2004 |
| WO | WO 2004/101071 | 11/2004 |
| WO | WO 2005/002649 | 1/2005 |
| WO | WO 2005/011779 | 2/2005 |
| WO | WO 2005/025652 | 3/2005 |
| WO | WO 2005/037185 | 4/2005 |
| WO | WO 2005/037350 | 4/2005 |
| WO | WO 2005/039673 | 5/2005 |
| WO | WO 2005/094919 | 10/2005 |
| WO | WO 2005/123186 | 12/2005 |
| WO | WO 2005/123189 | 12/2005 |
| WO | WO 2006/060277 | 6/2006 |
| WO | WO 2006/067217 | 6/2006 |
| WO | WO 2006/077263 | 7/2006 |
| WO | WO 2006/089958 | 8/2006 |
| WO | WO 2006/120253 | 11/2006 |
| WO | WO 2006/123329 | 11/2006 |
| WO | WO 2007/122207 | 11/2007 |
| WO | WO 2009/021950 | 2/2009 |

OTHER PUBLICATIONS

International Preliminary Examination Report issued in connection with counterpart PCT Application No. PCT/EP2006/062301, mailed Nov. 22, 2007.
International Search Report and Written Opinion issued in connection with counterpart international application No. PCT/EP2006/062301, mailed Nov. 2, 2006.
International Search Report mailed May 24, 2006 in international application No. PCT/EP2006/050410.
Office Action Issued in Connection With Counterpart Danish Application No. PA 2005 00703, Mailed Mar. 3, 2006.
CN 1612758 English Abstract, published Feb. 6, 2008.
DE 10255817 English Abstract, published Jun. 17, 2004.
DE 2552446 English Abstract, published May 26, 1977.
JP 2002-505601 Machine Translation, published Feb. 19, 2002.
JP 2000-515394 Machine Translation, published Nov. 21, 2000.
JP 2000-513259 Machine Translation, published Oct. 10, 2000.
JP 2000-104659 Machine Translation, published Apr. 11, 2000.
Final Office Action mailed Apr. 16, 2010 in U.S. Appl. No. 12/303,307, filed Feb. 20, 2009 by Krag.
Non-Final Office Action mailed Nov. 27, 2009 in U.S. Appl. No. 12/303,307, filed Feb. 20, 2009 by Krag.
Non-Final Office Action mailed Apr. 6, 2010 in U.S. Appl. No. 12/298,253, filed Dec. 8, 2008 by Krag et al.
Final Office Action mailed Apr. 28, 2010 in U.S. Appl. No. 12/066,712, filed Mar. 13, 2008 by Hansen et al.
Non-Final Office Action mailed Oct. 27, 2009 in U.S. Appl. No. 12/066,712, filed Mar. 13, 2008 by Hansen et al.
Non-Final Office Action mailed Apr. 10, 2009 in U.S. Appl. No. 12/066,712, filed Mar. 13, 2008 by Hansen et al.
Final Office Action mailed Jul. 16, 2010 in U.S. Appl. No. 11/913,689, filed Dec. 12, 2007 by Hansen et al.
Non-Final Office Action mailed Mar. 15, 2010 in U.S. Appl. No. 11/913,689, filed Dec. 12, 2007 by Hansen et al.
Final Office Action mailed Nov. 25, 2009 in U.S. Appl. No. 11/913,689, filed Dec. 12, 2007 by Hansen et al.
Non-Final Office Action mailed May 8, 2009 in U.S. Appl. No. 11/913,689, filed Dec. 12, 2007 by Hansen et al.
Non-Final Office Action mailed Apr. 30, 2010 in U.S. Appl. No. 11/911,213, filed Oct. 11, 2007 by Nielsen et al.
Non-Final Office Action mailed Jul. 24, 2009 in U.S. Appl. No. 11/911,213, filed Oct. 11, 2007 by Nielsen et al.
Final Office Action mailed Nov. 17, 2009 in U.S. Appl. No. 11/816,729, filed Nov. 15, 2007 by Larsen et al.
Non-Final Office Action mailed Apr. 17, 2009 in U.S. Appl. No. 11/816,729, filed Nov. 15, 2007 by Larsen et al.
Non-Final Office Action mailed Jul. 23, 2010 in U.S. Appl. No. 11/813,433, filed Apr. 30, 2008 by Teisen-Simony et al.
Non-Final Office Action mailed Apr. 28, 2010 in U.S. Appl. No. 11/813,381, filed Apr. 11, 20008 by Teisen-Simony et al.
Final Office Action mailed Nov. 3, 2009 in U.S. Appl. No. 11/792,355, filed Apr. 23, 2008 by Ethelfeld et al.
Non-Final Office Action mailed Feb. 17, 2009 in U.S. Appl. No. 11/792,355, filed Apr. 23, 2008 by Ethelfeld et al.
Final Office Action mailed Dec. 29, 2009 in U.S. Appl. No. 11/663,048, filed Nov. 15, 2007 by Thorkild et al.
Non-Final Office Action mailed Apr. 17, 2009 in U.S. Appl. No. 11/663,048, filed Nov. 15, 2007 by Thorkild et al.

(56) References Cited

OTHER PUBLICATIONS

Notice of Abandonment mailed Oct. 23, 2007 in U.S. Appl. No. 11/662,905, filed Sep. 22, 2005 by Ahm et al.
Non-Final Office Action mailed May 19, 2010 in U.S. Appl. No. 11/541,348, filed Sep. 29, 2006 by Preuthun et al.
Final Office Action mailed Jan. 8, 2010 in U.S. Appl. No. 11/541,348, filed Sep. 29, 2006 by Preuthun et al.
Non-Final Office Action mailed May 22, 2009 in U.S. Appl. No. 11/541,348, filed Sep. 29, 2006 by Preuthun et al.
Response and Amendment filed Jan. 29, 2009 in U.S. Appl. No. 11/541,348, filed Sep. 29, 2006 by Preuthun et al.
Final Office Action mailed Oct. 29, 2008 in U.S. Appl. No. 11/541,348, filed Sep. 29, 2006 by Preuthun et al.
Response and Amendment filed Jul. 16, 2008 in U.S. Appl. No. 11/541,348, filed Sep. 29, 2006 by Preuthun et al.
Non-Final Office Action mailed Apr. 18, 2008 in U.S. Appl. No. 11/541,348, filed Sep. 29, 2006 by Preuthun et al.
Final Office Action mailed May 5, 2010 in U.S. Appl. No. 11/540,842, filed Sep. 29, 2006 by Preuthun et al.
Non-Final Office Action mailed Sep. 28, 2009 in U.S. Appl. No. 11/540,842, filed Sep. 29, 2006 by Preuthun et al.
Response and Amendment filed Aug. 7, 2009 in U.S. Appl. No. 11/540,842, filed Sep. 29, 2006 by Preuthun et al.
Final Office Action mailed May 13, 2009 in U.S. Appl. No. 11/540,842, filed Sep. 29, 2006 by Preuthun et al.
Response and Amendment filed Mar. 11, 2009 in U.S. Appl. No. 11/540,842, filed Sep. 29, 2006 by Preuthun et al.
Non-Final Office Action mailed Dec. 12, 2008 in U.S. Appl. No. 11/540,842, filed Sep. 29, 2006 by Preuthun et al.
Response and Amendment filed Oct. 10, 2008 in U.S. Appl. No. 11/540,842, filed Sep. 29, 2006 by Preuthun et al.
Final Office Action mailed Jul. 11, 2008 in U.S. Appl. No. 11/540,842, filed Sep. 29, 2006 by Preuthun et al.
Response and Amendment filed May 20, 2008 in U.S. Appl. No. 11/540,842, filed Sep. 29, 2006 by Preuthun et al.
Non-Final Office Action mailed Feb. 25, 2008 in U.S. Appl. No. 11/540,842, filed Sep. 29, 2006 by Preuthun et al.
Final Office Action mailed Aug. 5, 2009 in U.S. Appl. No. 11/407,647, filed Apr. 20, 2006 by Hansen et al.
Non-Final Office Action mailed Feb. 6, 2009 in U.S. Appl. No. 11/407,647, filed Apr. 20, 2006 by Hansen et al.
Final Office Action mailed Sep. 29, 2008 in U.S. Appl. No. 11/407,647, filed Apr. 20, 2006 by Hansen et al.
Non-Final Office Action mailed Feb. 28, 2008 in U.S. Appl. No. 11/407,647, filed Apr. 20, 2006 by Hansen et al.
Non-Final Office Action mailed Aug. 19, 2010 in U.S. Appl. No. 11/266,905, filed Nov. 4, 2005 by Ethelfeld et al.
Final Office Action mailed Oct. 30, 2009 in U.S. Appl. No. 11/266,905, filed Nov. 4, 2005 by Ethelfeld et al.
Non-Final Office Action mailed Mar. 18, 2009 in U.S. Appl. No. 11/266,905, filed Nov. 4, 2005 by Ethelfeld et al.
Non-Final Office Action mailed Aug. 25, 2008 in U.S. Appl. No. 11/266,905, filed Nov. 4, 2005 by Ethelfeld et al.
Final Office Action mailed Oct. 5, 2007 in U.S. Appl. No. 11/266,905, filed Nov. 4, 2005 by Ethelfeld et al.
Non-Final Office Action mailed Mar. 27, 2007 in U.S. Appl. No. 11/266,905, filed Nov. 4, 2011 by Ethelfeld et al.
Notice of Abandonment mailed Oct. 12, 2010 in U.S. Appl. No. 11/266,904, filed Nov. 4, 2005 by Ethelfeld et al.
Second Advisory Action mailed Aug. 13, 2008 in U.S. Appl. No. 11/266,904, filed Nov. 4, 2005 by Ethelfeld et al.
First Advisory Action mailed Dec. 28, 2007 in U.S. Appl. No. 11/266,904, filed Nov. 4, 2005 by Ethelfeld et al.
Final Office Action mailed Sep. 11, 2007 in U.S. Appl. No. 11/266,904, filed Nov. 4, 2005 by Ethelfeld et al.
Non-Final Office Action mailed Jan. 5, 2007 in U.S. Appl. No. 11/266,904, filed Nov. 4, 2005 by Ethelfeld et al.
Requirement for Restriction mailed May 22, 2006 in U.S. Appl. No. 11/266,904, filed Nov. 4, 2005 by Ethelfeld et al.
Notice of Allowance mailed Jul. 15, 2009 in U.S. Appl. No. 11/266,821, filed Nov. 4, 2005 by Ethelfeld et al.
Non-Final Office Action mailed Jan. 29, 2009 in U.S. Appl. No. 11/266,821, filed Nov. 4, 2005 by Ethelfeld et al.
Final Office Action mailed Jul. 18, 2008 in U.S. Appl. No. 11/266,821, filed Nov. 4, 2005 by Ethelfeld et al.
Non-Final Office Action mailed Mar. 28, 2008 in U.S. Appl. No. 11/266,821, filed Nov. 4, 2005 by Ethelfeld et al.
Final Office Action mailed Oct. 16, 2009 in U.S. Appl. No. 11/250,233, filed Oct. 14, 2005 by Ethelfeld et al.
Non-Final Office Action mailed Mar. 12, 2009 in U.S. Appl. No. 11/250,233, filed Oct. 14, 2005 by Ethelfeld et al.
Notice of Abandonment mailed Aug. 31, 2010 in U.S. Appl. No. 10/566,795, filed Aug. 30, 2006 by Radmer et al.
Final Office Action mailed May 4, 2009 in U.S. Appl. No. 10/566,795, filed Aug. 30, 2006 by Radmer et al.
Non-Final Office Action mailed Oct. 17, 2008 in U.S. Appl. No. 10/566,795, filed Aug. 30, 2006 by Radmer et al.
US 6,197,009, 03/2001, Steg (withdrawn)

* cited by examiner

NON-POROUS MATERIAL AS STERILIZATION BARRIER

CROSS-REFERENCE TO RELATED APPLICATIONS

This application is a 35 U.S.C. §371 national stage application of International Patent Application PCT/EP2008/064762 (published as WO2009/056616), filed Oct. 31, 2008, which claimed priority of European Patent Application 07119760.2, filed Oct. 31, 2007; this application further claims priority under 35 U.S.C. §119 of U.S. Provisional Application 60/985,301, filed Nov. 5, 2007.

The present invention relates to articles and devices comprising an enclosure with a sealed interior, at least a portion of the enclosure serving as a sterilization barrier, this allowing the interior to be sterilized, as well as methods for sterilizing such devices. The enclosure may be provided with an opening covered by a sterilization barrier.

BACKGROUND OF THE INVENTION

When gas-sterilizing medical products, e.g. using water vapour (steam), it is necessary to encapsulate the product in such a way that on one hand steam may enter (and thus sterilize) the product and on the other hand the product remains sterile after sterilization. Normally this is achieved using a sterilization barrier in form of a specialised moist penetratable porous sheet material forming at least part of the packaging material. For example, U.S. Pat. No. 6,808,691 discloses sheets for sealable sterilizing packages based on cellulose fibres (e.g. paper), paper sheets reinforced by synthetic fibres mixed with the cellulose fibres, as well as non-woven sheets obtained by a dry route and comprising only hot-bonded synthetic fibres. Also micro-porous polymeric foils have been developed. In case sterilization takes place using radiation WO 02/070024 discloses a method in which a bioactive material is enclosed in a package, the package being formed from a non-porous material allowing sterilizing radiation to penetrate yet prevents an enclosed hydrogen gas scavenger to escape.

If the entire product is to be gas sterilized the product can be placed in a pouch or bag being fully or partly penetratable to the sterilizing gas, however, if only the interior of a given product is to be sterilized and the product comprises one or more openings, then these openings can be sealed by attaching planar sheets of sterilization barrier material by e.g. welding or gluing, this allowing the interior of the product to be sterilized through the one or more openings.

To sterilize the products (either in the form of bagged items such as pharmaceutical closures, or products with a sealed interior), a vacuum autoclave must normally be used because air trapped in the bag or interior must first be removed since it inhibits the process of steam sterilization. As described in U.S. Pat. No. 6,818,178, to achieve air removal, a vacuum steam autoclave typically subjects its contents to a conditioning or pre-vacuum phase in which the autoclave environment undergoes a series of alternating vacuum and steam cycles to remove air from the autoclave and the interior of the stopper bags. Three or four pulses are usually employed, each drawing a vacuum on the autoclave chamber and then introducing steam until the chamber reaches a predetermined positive pressure when the admission of steam is stopped and a vacuum is once again drawn. This type of pulsing is known to provide the greatest efficiency in quickly effecting the desired removal of air prior to sterilization.

Although sterilization barriers in the form of sheet materials are relatively inexpensive and thus attractive for many applications, they are difficult to use if they have to be formed to cover a non-planar opening or a projecting member. Correspondingly, it may be necessary to add an opening to a given product for the sole purpose of providing a sterilization barrier.

Having regard to the above-identified problems, it is an object of the present invention to provide a device comprising a sealed interior and an opening covered by a sterilization barrier, wherein the sterilization barrier allows the device to be manufactured in a cost-effective matter yet provides and high degree of design freedom for the device as such.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect of the invention provides a device comprising a sealed interior portion with at least one opening covered by a sterilization barrier formed from a non-porous material allowing a sterilization gas to penetrate but prevents germs from penetrating. The size and configuration of the at least one sterilization barrier formed from a non-porous material are adapted to allow at least 50% of the sterilization gas, that would pass between a sterilization gas-containing exterior and the sealed interior portion when a pressure difference is created there between, to pass through the non-porous material.

By the term "non-porous" is to be understood a material generally having no "openings" in which molecules of a sterilization gas can pass, i.e. any passing molecule (e.g. water molecules in the case of steam) will have to pass by diffusion between the molecules of the non-porous material. Although such a material can be characterized as being gas penetratable, the gas will in general pass by molecular diffusion. In a porous material having openings the size of the openings is much larger than the distance between the molecules in the porous material and also the size of the gas molecules, this allowing a gas to penetrate in gaseous form.

The definition of "at least 50%" in respect of sterilization gas penetration through the non-porous material provides that the present invention is differentiated from being accidentally anticipated by prior art in which a sealed interior is closed by a conventional porous sterilization barrier, but where a small amount of sterilization gas un-intended may pass through portions of the device made from a non-porous material as in the present invention. The present invention is thus based on the discovery that a non-porous material can be used intentionally as a sterilization barrier for a gas. Indeed, most of the non-porous materials that would be considered for use as a sterilization barrier (e.g. Liquid Silicone Rubber—LSR) have gas permeabilities that are lower than conventional sterilization barrier materials such as paper. Correspondingly, when designing a given device in accordance with the present invention a number of parameters should be taken into account, e.g. the interior volume to be sterilized, and the area and thickness of the non-porous sterilization barrier. For example, in case a given device has both a small and a large sealed interior portion it may be desirable to provide the smaller portion with a non-porous sterilization barrier in accordance with the present invention, and provide the larger portion with a traditional porous sterilization barrier. As appears, the size and configuration of the at least one sterilization barrier formed from a non-porous material as well as the design of the remaining device may be adapted to allow sterilization gas passage through the non-porous material at any desired percentage in the 50-100% range, e.g. 80%, 90% or 95%.

The device may comprise a further sealed interior portion with at least one opening covered by a sterilization barrier formed from a porous material allowing a sterilization gas to penetrate but prevents germs from penetrating.

In an exemplary embodiment the device comprises a flow path arranged between an inlet and an outlet. The device may be in the form of a pump with a flow path arranged between the inlet and the outlet, with the pump comprising at least one valve member arranged in the flow path. Such a valve may be used to form a barrier between two sealed interior portions, e.g. sealed by a porous respectively a non-porous sterilization barrier. At least one sterilization barrier formed from non-porous material may be moulded in a non-planar configuration, thereby providing a barrier configuration which is more difficult to achieve using traditional barrier materials such as paper.

The device may comprise an opening in the form of a tubular member projecting from the device, and wherein a non-planar sterilization barrier formed from non-porous material is moulded in a tubular configuration covering at least a distal portion of the tubular member. For example, the tubular member may be in the form of a pointed hollow needle covered by a tubular barrier member moulded fully or partly in a LSR-containing material. When the device is provided in combination with a fluid source adapted to engage the protruding tubular member, such a tubular sterilization barrier may be adapted to collapse around the tubular member as the latter is connected to the fluid source, e.g. inserted through a septum member of a fluid drug reservoir.

In a further aspect a method is provided comprising the steps of (i) providing a device comprising (a) a sealed interior portion with at least one opening covered by a sterilization barrier formed from a non-porous material allowing a sterilization gas to penetrate but prevents germs from penetrating, wherein (b) the size and configuration of the at least one sterilization barrier formed from a non-porous material allow at least 50% of the sterilization gas, that would pass between a sterilization gas-containing exterior and the sealed interior portion when a pressure difference is created there between, to pass through the non-porous material, (ii) placing the device in a sterilization enclosure, (iii) creating a relative vacuum in the sealed interior portion by controlling the pressure in the sterilization enclosure, (iv) introducing sterilization gas in the sterilization enclosure thereby raising the pressure therein above the relative vacuum created in the sealed interior portion, and (v) allowing the sterilization gas to penetrate into the sealed interior portion, whereby at least 50% of the sterilization gas passes between the sterilization enclosure and the sealed interior portion through the at least one sterilization barrier formed from a non-porous material.

As described above, the non-porous material may be LSR or polymeric blends comprising LSR and it may be moulded in a non-planar configuration. The sterilization gas may be steam.

In the context of the present application the term relative humidity (RH) is used, this being defined as the ratio of the partial pressure of water vapor in a gaseous mixture of air and water to the saturated vapor pressure of water at a given temperature, and expressed as a percentage.

As used herein, the term "drug" is meant to encompass any drug-containing flowable medicine capable of being passed through a delivery means such as a hollow needle in a controlled manner, such as a liquid, solution, gel or fine suspension. Representative drugs include pharmaceuticals such as peptides, proteins, and hormones, biologically derived or active agents, hormonal and gene based agents, nutritional formulas and other substances in both solid (dispensed) or liquid form. In the description of the exemplary embodiments reference will be made to the use of insulin. Correspondingly, the term "subcutaneous" infusion is meant to encompass any method of transcutaneous delivery to a subject.

BRIEF DESCRIPTION OF THE DRAWINGS

In the following the invention will be further described with reference to the drawings, wherein.

DESCRIPTION OF EXEMPLARY EMBODIMENTS

When in the following terms such as "upper" and "lower", "right" and "left", "horizontal" and "vertical" or similar relative expressions are used, these only refer to the appended figures and not to an actual situation of use. The shown figures are schematic representations for which reason the configuration of the different structures as well as there relative dimensions are intended to serve illustrative purposes only.

Figure 1:
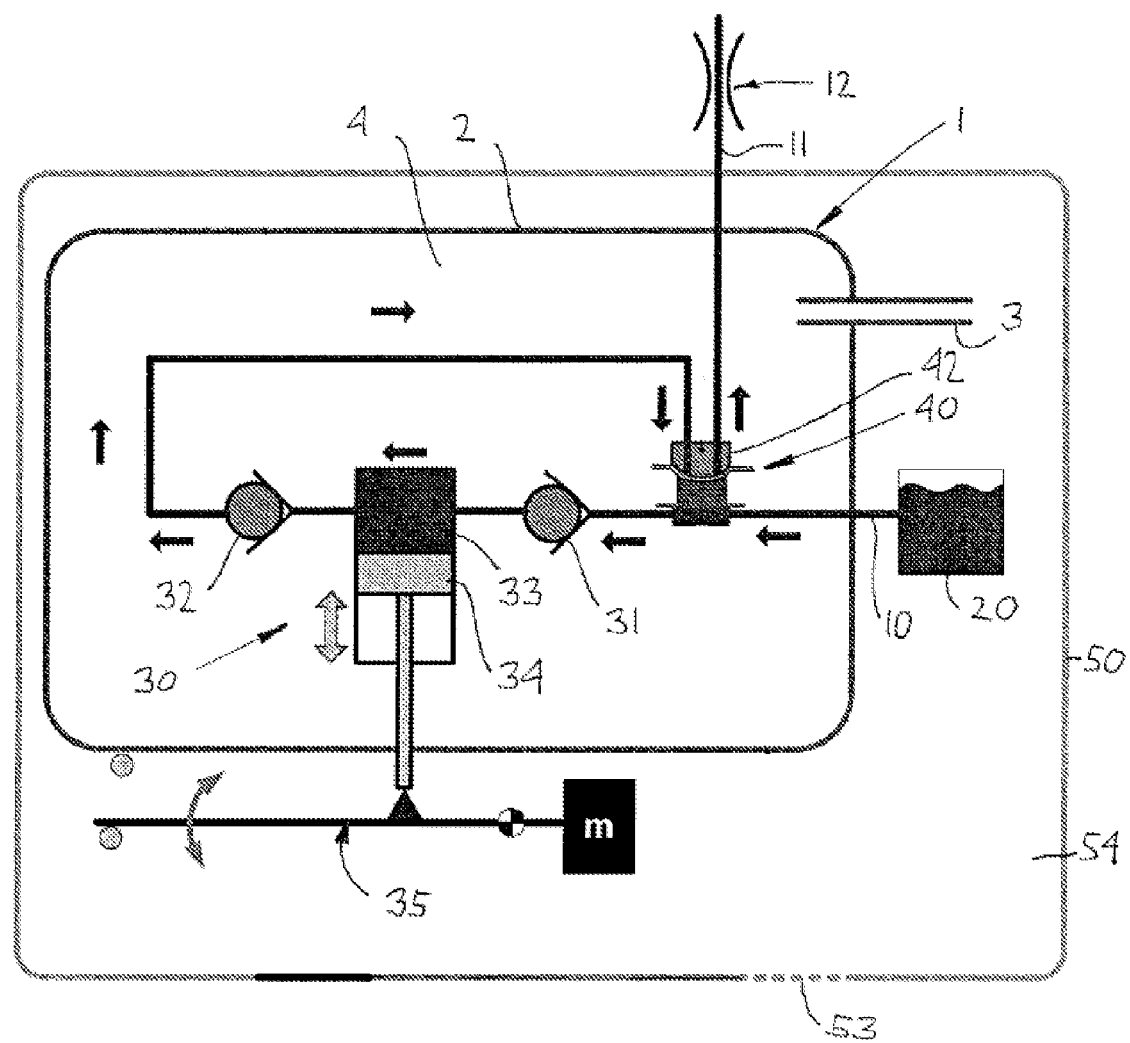
FIG. 1 shows a schematic overview of a pump assembly connected to a reservoir.

With reference to FIG. 1 a schematic overview of a pump system 1 connected to a reservoir 20 is shown, the pump system comprising the following general features: a fluid inlet 10 in fluid communication with the reservoir 20, a suction pump 30 per se having inlet and outlet valves 31, 32 and a pump chamber 33 with an associated piston 34 driven by an actuator 35, an outlet 11 connected to e.g. an infusion patch 12, and a combined safety valve 40. The combined safety valve has a primary side with the pressure in the inlet 10 acting on a piston 41 which again acts on an anti-suction membrane valve 42, this valve allowing a positive-pressure flow of fluid across the valve but does not allow a flow of fluid due to suction, e.g. as may be applied to outlet 11. The arrows indicate the flow direction between the individual components. The pump system further comprises a housing 2 with a vent 3, this establishing a vented enclosure 4 in which the above-described components (apart from the reservoir) are arranged. In the shown embodiment an outer housing 50 comprising a second vent 53 (e.g. in the form of a Gore-Tex® membrane) is provided, this establishing a vented enclosure 54 for the pump assembly.

When the piston is moved downwards (in the drawing) a relative negative pressure will build up inside the pump chamber which will cause the inlet valve to open and subsequently fluid will be drawn form the reservoir through the open primary side of the safety valve by suction action. When the piston is moved upwards (in the drawing) a relative overpressure will build up in the pump chamber which will cause the inlet valve to close and the outlet valve and the safety valve to open whereby fluid will flow from the pump chamber through the outlet valve and the secondary side of the safety valve to the outlet. As appears, in normal operation the combined safety valve allows fluid passage during both intake and expelling of fluid and is thus "passive" during normal operation. However, in case the reservoir is pressurized (as may happen for a flexible reservoir) the elevated pressure in the reservoir will be transmitted to both the primary side of the safety valve and, via the pump chamber, the secondary side of the safety valve in which case the pressure on the primary side of the safety valve will prevent the secondary side to open due to e.g. the pressure drop across the inlet and outlet valves.

Figure 2:
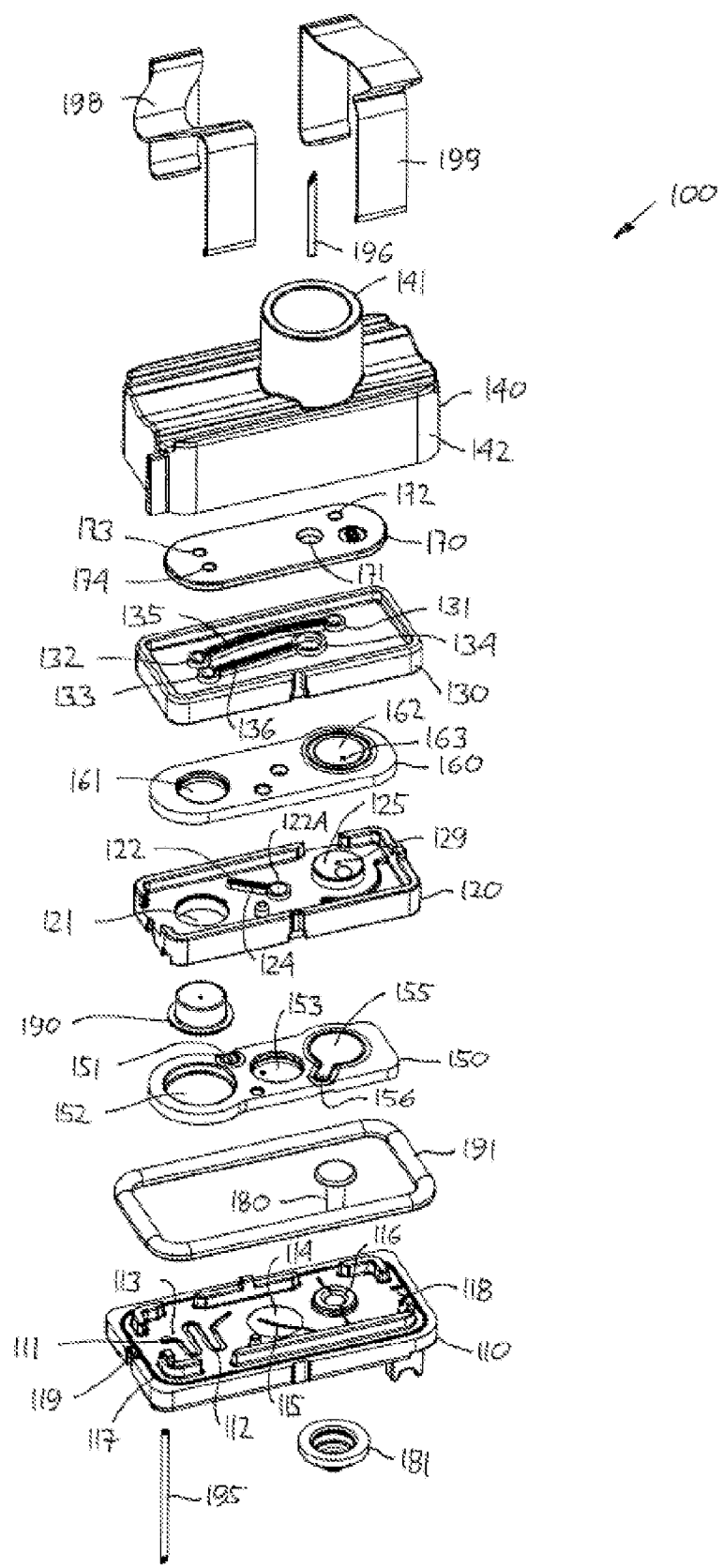
FIGS. 2 and 3 show exploded views of a pump assembly.
Figure 3:
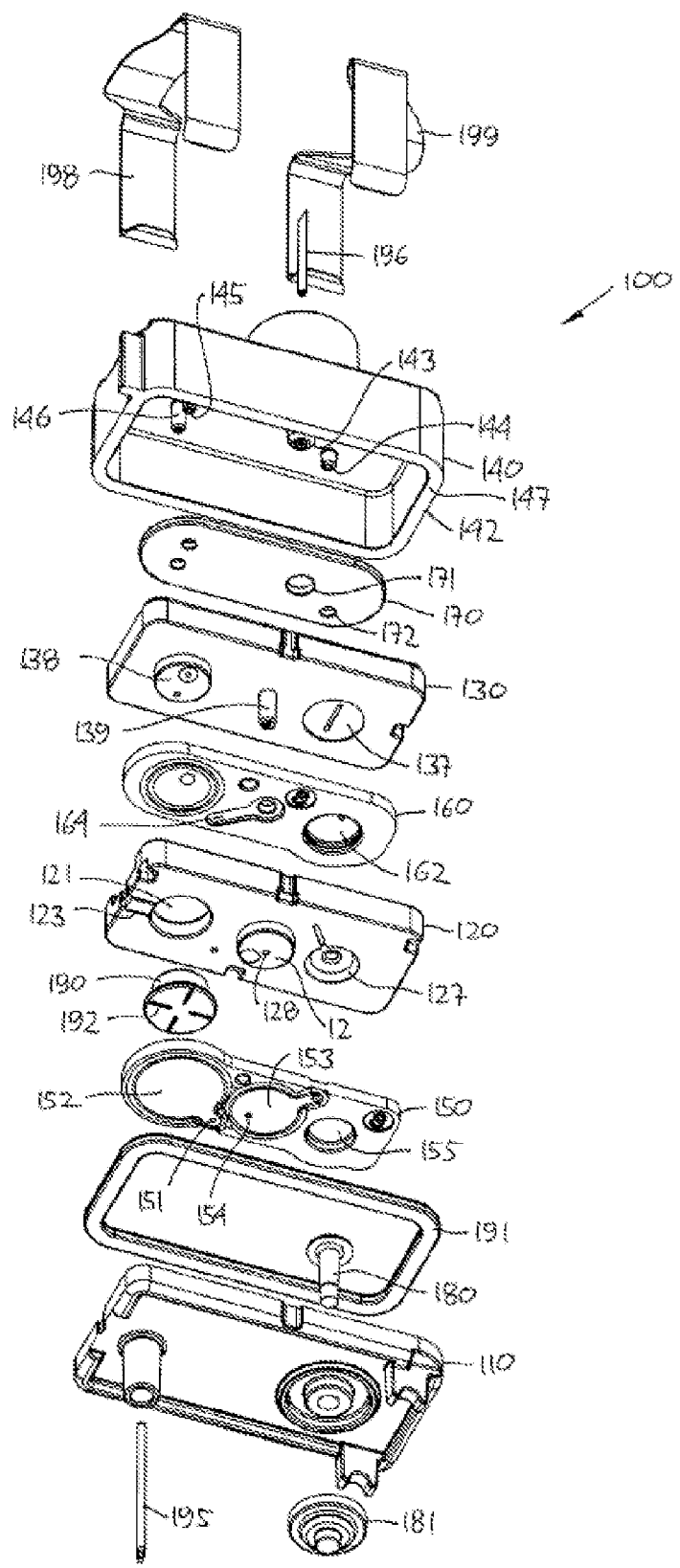

In FIGS. 2 and 3 an exploded view (seen from above respectively below) of a pump system 100 utilizing the pump principle depicted in FIG. 1 is shown, the pump system being suitable for use with e.g. a flexible reservoir. The system comprises a pump assembly (i.e. a pump per se) with an integrated housing. The pump is a membrane pump comprising a piston-actuated pump membrane with flow-controlled inlet- and outlet-valves. The pump has a general layered construction comprising rigid plates in the form of a bottom plate 110, a middle plate 120, a top plate B 130, and a top plate A 140 between which are interposed flexible membrane members in the form of (from below) a second membrane 150, a first membrane 160, and a third membrane 170. The pump further comprises a piston 180 interposed between the bottom plate and the second membrane, a piston gasket 181 arranged between the piston stem and the bottom plate, a safety valve piston 190 arranged in the middle plate and interposed between the first and second membrane, a main gasket 191 interposed between the skirt 142 of top plate A and the bottom plate, and inlet and outlet conduits 195, 196 in the form of pointed hollow needles. The layers are held in a stacked arrangement by outer clips 198, 199. The pump is supplied to a user in a sterile state with a needle penetratable tubular elastomeric sealing member 197 covering the inlet needle 195 and a penetratable paper seal 193 (see FIG. 4) covering the outlet conduit. This design allows the tubular sealing member to be penetrated and collapse when the needle 197 is pushed into engagement with a fluid source, e.g. a drug reservoir.

Next the different functional components of the individual members will be described with reference to FIGS. 2 and 3, the members having an "upper" surface facing in direction of the outlet and a "lower" surface facing in direction of the inlet. In general the different valves each comprise a valve seat across which a first surface of a flexible valve membrane is arranged, a valve cavity being formed between the second surface of the valve membrane and an opposed valve wall or valve "roof". Depending on the function of the valve, openings may be formed in the valve seat and valve membrane. Apart from the primary side safety valve membrane, all the valve membranes are tensioned against the corresponding valve seat thus requiring a given pressure differential across the valve in order to open. The top plates comprise a number of cylindrical core members with an outer channel along there length, however, these core members are only provided for the cost-effective manufacture of fine bores in the members through which they are arranged.

The bottom plate 110 comprises an upper surface with an inlet bore 111 in flow communication with a serpentine channel 112 arranged across a first safety valve seat 113, an inlet valve wall 114 with a transfer channel 115, a piston bore 116 for the piston stem, an open circumferential channel 117 having an inlet channel 118 and an opposed outlet 119, and on the lower surface mounting means for an actuator.

The second membrane 150 comprises a bore 151, a primary side safety valve membrane 152, an inlet valve membrane 153 with an opening 154, and a pump membrane 155 in communication with a bore 156.

The middle plate 120 comprises a piston bore 121 for the safety valve piston 190, first and second bores 122, 122A, an upper surface with a transfer channel 124 interconnecting the first and second bores, and an outlet valve seat 125, a lover surface with an inlet valve seat 126, a pump cavity 127, and a pair of vent channels 123 between the piston bore and the exterior. The inlet valve seat comprises an opening 128 in communication with the second bore 122A, just as a bore 129 connects the pump cavity and the outlet valve seat 125.

The first membrane 160 comprises a secondary side safety valve membrane 161, an outlet valve membrane 162 with an opening 163, an opening for a core member 139, and a lover surface with a channel 164 adapted to engage the transfer channel 124.

The top plate B 130 comprises first, second and third bores 131, 132, 133 as well as partial bore 134, an upper surface with a curved first transfer channel 135 interconnecting the first and second bores, and a straight second transfer channel 136 interconnecting the third bore and the partial bore, a lover surface with an outlet valve wall 137 having an opening in flow communication with the first bore 131, a second safety valve seat 138 having first and second openings in flow communications with the second respectively third bores 132, 133, and a core member 139 adapted to engage the middle plate 120.

The third membrane 170 comprises an outlet bore 171 adapted to receive a core member 143, three openings 172, 173, 174 for core members 144, 145, 146, and a substantially planar lower surface adapted to engage the first and second channels in the top plate B.

The top plate A 140 comprises an outlet bore adapted to receive the outlet conduit 196, an upper surface with a cylindrical member 141 surrounding the outlet conduit, a lower surface with a circumferential skirt 142 having a circumferential lower edge 147, a first core member 143 comprising the outlet bore and adapted to be received in the partial bore 134 of the top plate A, and three further core members 144, 145, 146 adapted to be received in the bores 131, 132, 133 of the top plate B. In case the outlet conduit is in the form of a blunt protruding member it may be formed integrally with the top plate A.

Figure 4:
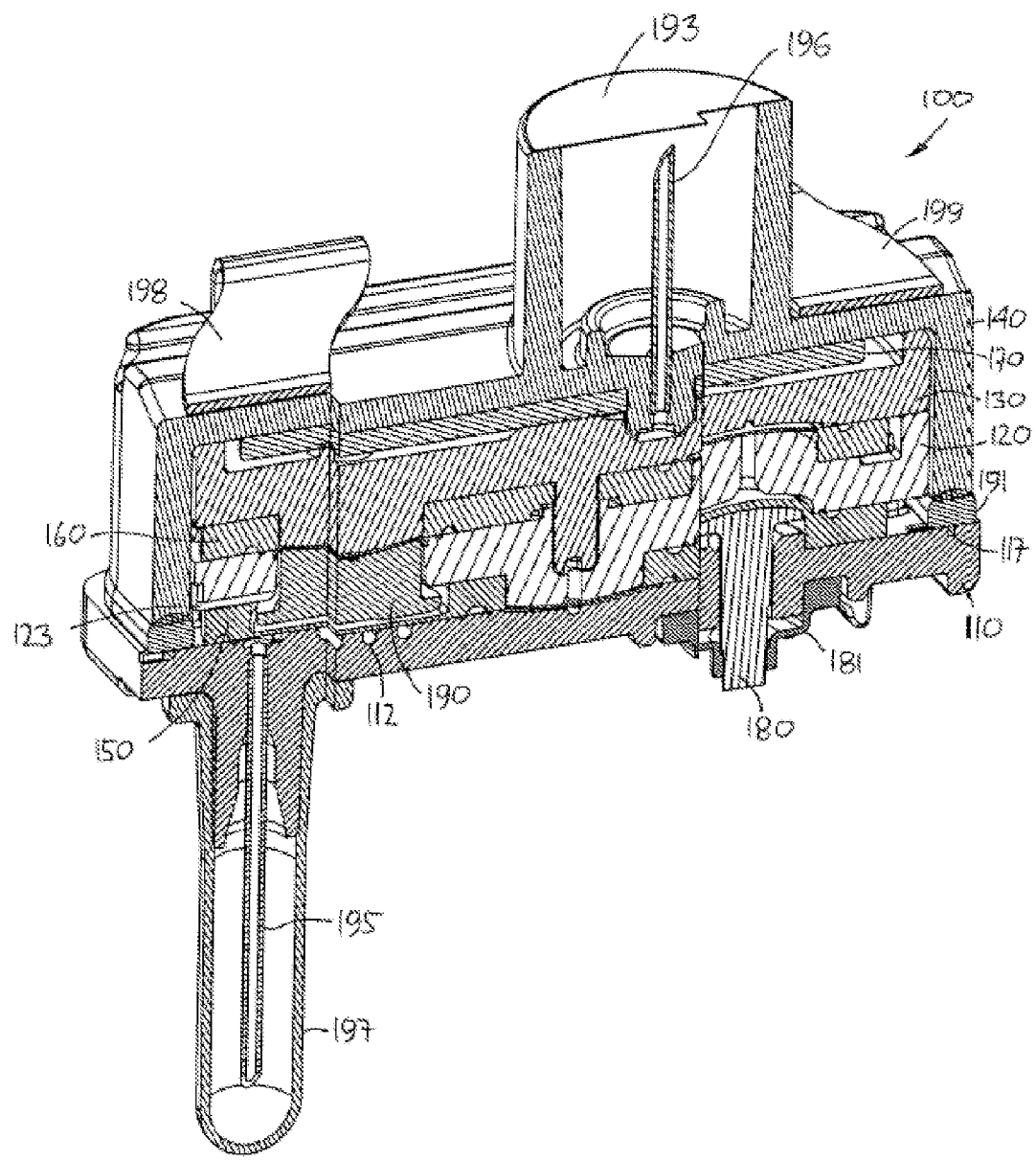
FIG. 4 shows a cross-sectional view of the pump assembly of FIG. 2 in an assembled state.

FIG. 4 shows a cross-sectional view of the pump system 100 of FIG. 2 in an assembled stacked state in which the four plates 110, 120, 130, 140, the three membranes 150, 160, 170, the piston 180, the safety valve piston 190 and the main gasket 191 can be seen together with many of the above-described structures. The circumferential lower edge 147 of the skirt 142 engages the upper surface of the bottom plate with the main gasket 191 interposed there between, this establishing an enclosure 194 for the remaining elements stacked between the bottom plate and the top plate A. As appears, apart from a narrow circumferential gap, the enclosed stacked elements almost occupy the enclosure. As also appears, the main gasket engages the circumferential channel 117 in the bottom plate and thus establishes a closed circumferential channel with an inlet channel 118 and an opposed outlet 119, this allowing the channel to serve as a vent. In the shown embodiment the housing is formed integrally with the bottom plate and the top plate A, however, the housing may also be provided as a separate structure.

Figure 5:
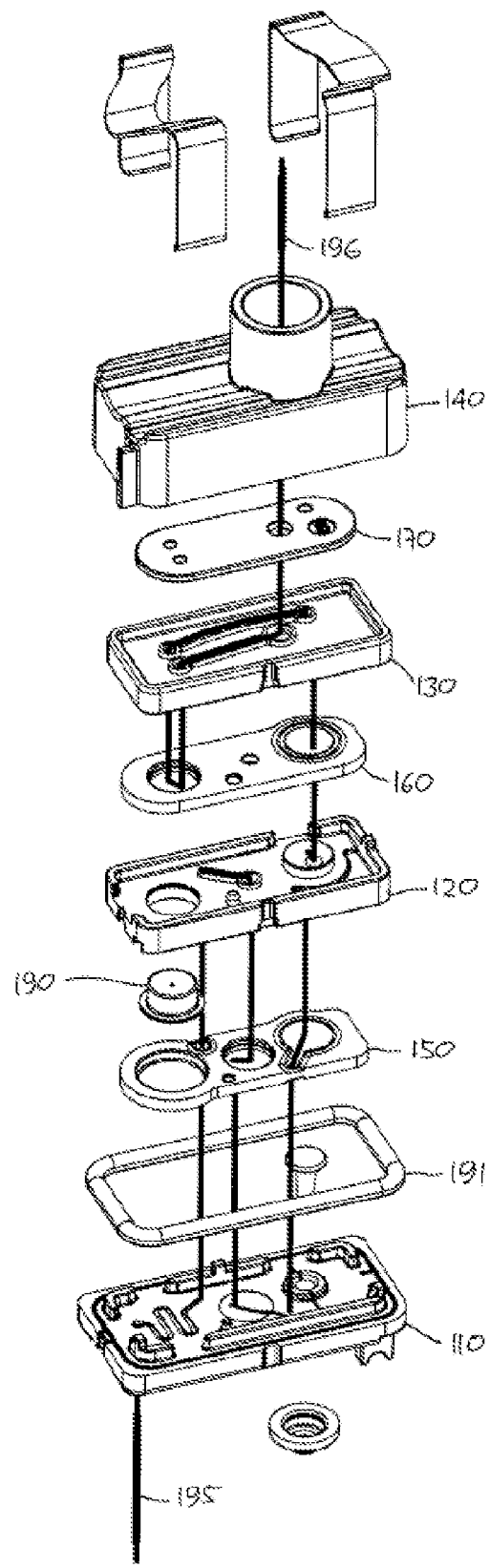
FIGS. 5 and 6 show the exploded views of FIGS. 2 and 3 with the flow path indicated.
Figure 6:
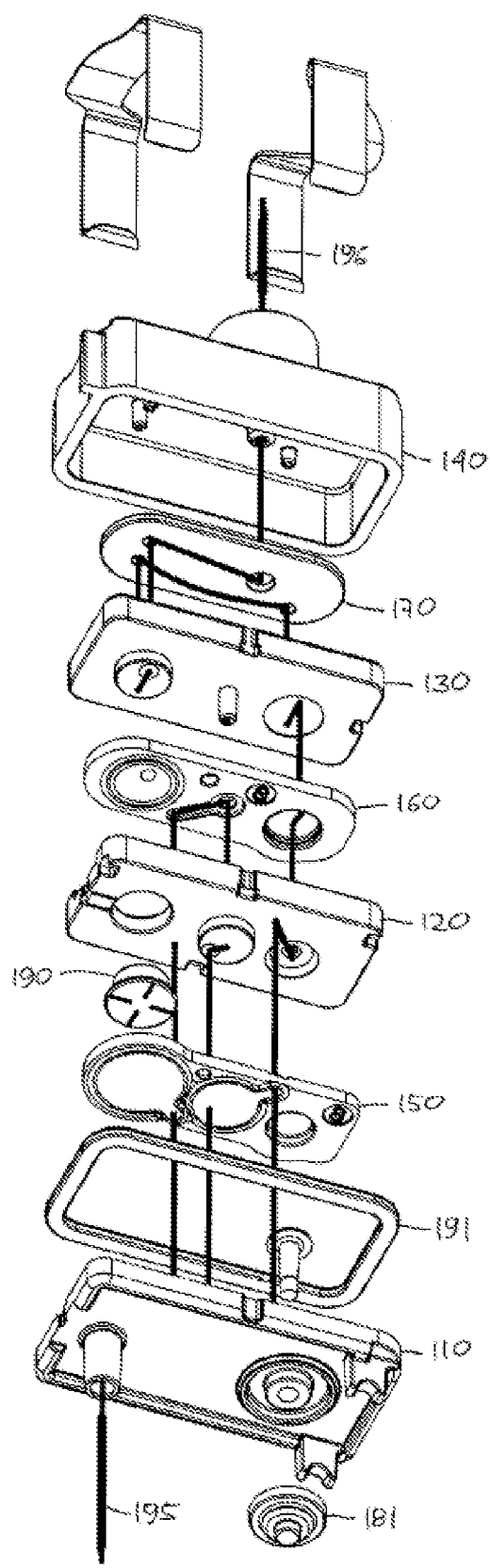

With reference to FIGS. 5 and 6 the flow path through the pump assembly will be described. FIGS. 5 and 6 essentially correspond to FIGS. 2 and 3 but with the flow path shown schematically. It should be noted that the shown flow path differs in the two figures as it has been drawn to illustrate flow across the surfaces actually shown, i.e. in FIG. 5 the flow path is shown corresponding to the upper surfaces and in FIG. 6 the flow path is shown corresponding to the lower surfaces.

Thus, fluid will enter (i.e. sucked into) the pump assembly 100 through the inlet conduit 195 and inlet bore 111, cross the first safety valve seat 113 along the serpentine channel 112 and enter the bores 151, 122 in the second membrane respectively the middle plate, flow through the transfer channel 124 to the inlet valve seat 126 via opening 128 where it crosses the valve seat and flows through the opening 154 in the inlet valve membrane 153. From the inlet valve the fluid will flow across the valve wall 114 along the transfer channel 115 and through bore 156 of the pump membrane 155 to the pump chamber 127 from where it will be pumped through the bore 129 to the outlet valve seat 125. The fluid will then cross the outlet valve seat and be forced through the opening 163 in the outlet valve membrane to the curved first transfer channel 135 via bore 131. The fluid will then cross the second safety valve seat 138 via bores 132, 133 and enter the straight second transfer channel 136 from where it will leave the pump assembly through the outlet bore of core member 143 and outlet conduit 196.

In normal operation the primary side safety valve membrane 152 will rest against the first safety valve seat 113 and the fluid will flow along the serpentine channel 112 without lifting the valve membrane. On the secondary side the secondary side safety valve membrane 161 will be lifted from the valve seat 138 as the fluid crosses from the first to the second transfer channel 135, 136 in top plate B. In case the fluid in the inlet is pressurized the primary side safety valve membrane will be lifted from its seat and move the safety piston 190 upwards against the secondary side safety valve membrane and thus close the secondary side safety valve. In principle the pressure should be the same on the two safety valve membranes, however, due to the pressure drop across the inlet and outlet valves as well as the opening pressure necessary to overcome the flow resistance of the pre-tensioned secondary side valve membrane, the pressure acting on the primary side of the safety piston will be higher than the pressure acting on its secondary side, this resulting in a closed safety valve. As also appears, in case suction is applied to the outlet side, this will close flow across the secondary side of the safety valve.

As described above with reference to FIGS. 1 and 4, the pump system comprises a housing with a vent, this establishing a vented enclosure for the pump per se. The main purpose of the vented housing is to create, in cooperation with one or more permeable membrane portions of the pump, a high RH micro-climate around the pump. This aspect of the described pump system is described in detail in co-pending application PCT/EP2008/060583 which is hereby incorporated by reference.

Turning to the sterilization aspect of the present invention, the above-described pump has a first sealed interior portion with an opening provided by the hollow needle 195 which is covered by a sterilization barrier in the form of tubular sealing member 197 formed from an elastomeric non-porous material allowing a sterilization gas to penetrate but prevents germs from penetrating. In the shown embodiment the tubular member is formed from Liquid Silicone Rubber (LSR) having the desired permeability to the preferred sterilization gas (i.e. steam) and allowing the seal to be formed in the desired shown form. The size and configuration (e.g. area and thickness) of the non-porous sterilization barrier are chosen to allow at least 50% of the sterilization gas to pass through the non-porous material. In the shown embodiment the first interior portion is formed between the distal end of the needle 195 and the inlet valve 153 which means that essentially all sterilizing gas will enter into the first interior portion through the tubular sealing member 197. The pump has a second sealed interior portion with an opening provided by the hollow needle 196 which is covered by a sterilization barrier in the form of sheet member 193 formed from a porous material allowing a sterilization gas to penetrate but prevents germs from penetrating. In the shown embodiment the sheet member is formed from conventional sterilization barrier paper. In the shown embodiment the second interior portion is formed between the distal end of the needle 196 and the secondary side safety valve membrane 161 which means that essentially all sterilizing gas will enter into the second interior portion through the tubular sealing member 197. In respect of sterilization of the interior portions arranged between the different valves reference is made to the below example.

In case the described pump did not have valves in its flow path such that a single interior space would be provided between the inlet and outlet, the pump would encompass the present invention if a sizeable amount of sterilization gas would enter the interior through the tubular sealing member 197.

EXAMPLE

Product design and materials: A pump of the general design described with reference to FIGS. 1-6 was used. As the inlet side of the pump is provided with a protruding inlet needle it would be difficult to design a sterile barrier using conventional materials such as Tyvek™ paper or the like. As an alternative the permeability of LSR (LR 3003/40 supplied by Wacker Chemie AG, Munich, Germany) was utilized. Although LSR permeability is less than for conventional barrier materials this was acceptable in the present case due to the volume of the pump being small at approximately 8 µl. For the outlet side barrier Tyvek™ paper was used.

The materials of the pump must be moist and heat stable. First priority is a sterilization temperature of 121° C. otherwise a lower temperature can be chosen if process parameters are changed and the process documented by $F_0$ calculations.

The accumulated diffusion of steam trough the needle cover during the pre-vacuum, heating and sterilization phase (see below) was calculated. During the drying phase the humidity/condensate from the steam must be replaced by sterile air. The diffusion of humidity in the drying phase was calculated. It was found that the maximum possibly penetration of humidity trough the materials were enough to ensure that moisture could come in contact with all interior surfaces of the product during sterilization and be removed during the drying phase.

Design of the sterilization program: Medical devices which are intended to be sterilized by moist heat must be designed to ensure that an adequate amount of moisture can penetrate the product. Selecting the primary packaging, which is an important part of the finished product, must be done with respect to the sterilization process. For moist heat it is important to look at the permeability of the barriers because of the need for penetration.

During design of the specific sterilization program all sterilization-related activities such as product design, packaging selection, sterilization cycle optimization etc. must be included. All this activities can/will have impact on the parameters for the final sterilization cycle, ensuring that an adequate amount of moisture at the proper temperature can be delivered for the required period of time to all sites requiring sterilization.

Design of the sterilization cycle must ensure that all air can be removed from the products and replaced by steam. Air can easily be removed in a vacuum autoclave and by the use of pre-vacuum pulses substantially all air can be removed in products with difficult designs.

Together all the above-mentioned physical properties should ensure germ lethality during the sterilization process. If no moisture on the product surfaces is present the consequence is a dry heat process which is an oxidation process with different kinetic from moist heat sterilization.

Dehydrated materials may cause superheating within the material itself because of the condensation on the surface. The moisture in the materials can be controlled by manufacturing the device in controlled environments (clean room) before they move to the terminal sterilization process.

Figure 7:
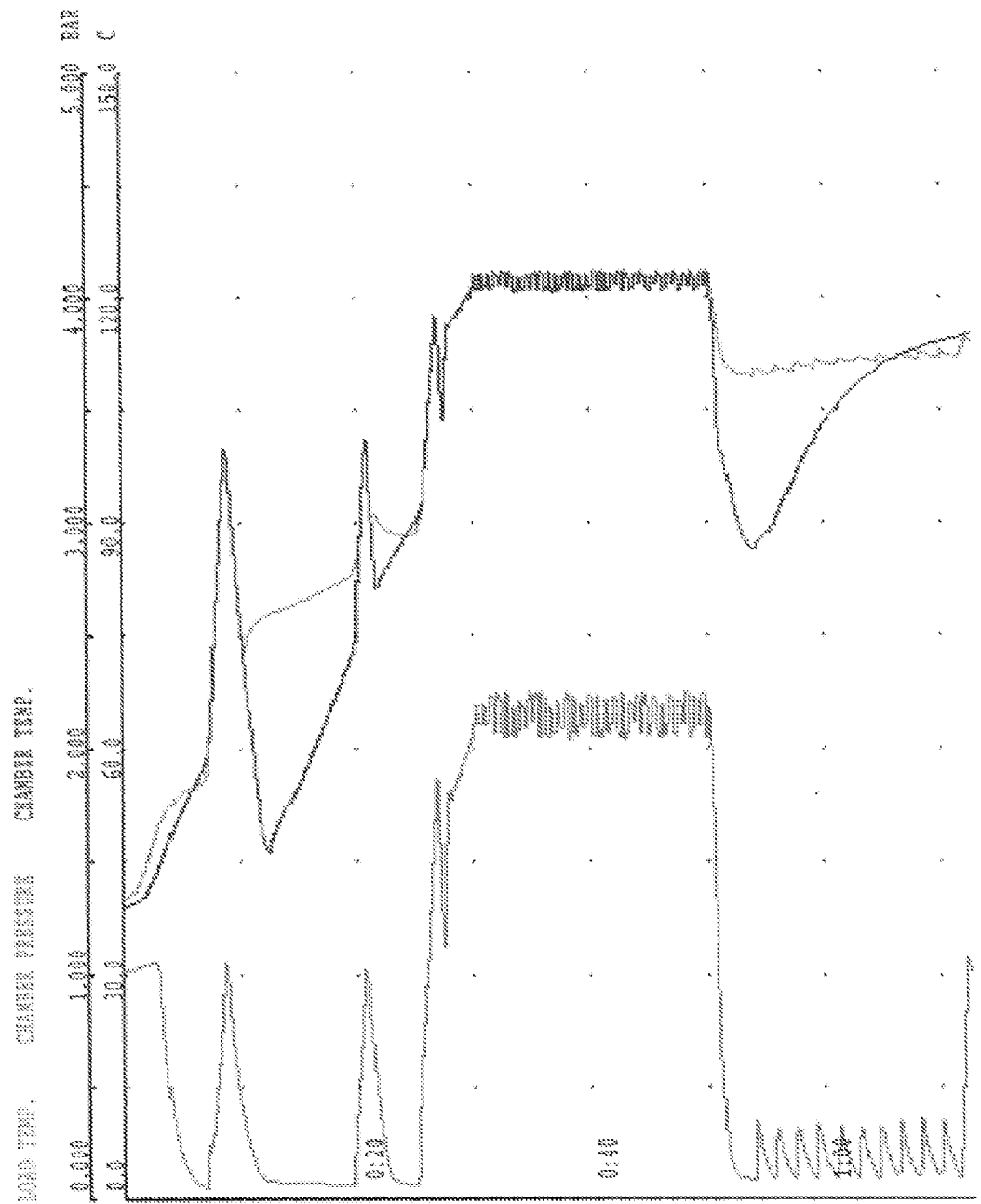
FIG. 7 shows a graph showing the realized chamber pressure and chamber temperature during a sterilization process.

Sterilization program: The above-described pump is a positive displacement pump with a check valve on each side of the pump chamber. Such a pump works when the pressure difference between the pump chamber and its surroundings changes. During normal work conditions this will be achieved by moving the piston forward and backwards causing compression or decompression of the pump chamber, but it may just as well be achieved by altering the ambient pressure. The sterilization program developed was designed such that the different interior spaces of the pump could be equally emptied from air and steam could be pumped through the pump. Several pressure changes are included in the evacuation phase, the sterilization phase and the drying phase to ensure inlet of steam and outlet of condensate during process. A graph showing the realized chamber pressure and chamber temperature is shown in FIG. 7. The program parameters used were as follows.

Pre-pulses 3
Pre-pulse bottom 0.070 bar
Pre-pulse top 1.050 bar
Pos. pulse 1
Pos. pulse top 1.850 bar
Pos. pulse bottom 1.200 bar
Sterilizing temp 121° C.
Sterilizing time 20 min
Sterilizing pulses 30
Sterilization pulse top 2.266 bar (realized)
Sterilization pulse bottom 2.065 bar (realized)
drying time 4 min
Post pulses 10
Post pulse top 0.352 bar (realized)
Post pulse bottom 0.085 bar (realized)

Test set-up: Steam penetration of the pump unit was tested by placement of suspension with *Geobacillus Stearothermophilus* inside the pump. Two types of BI inoculation methods were used for the test. For both types of inoculation *Geobacillus Stearothermophilus* was used as test organism. Totally 9 pump units were prepared: Four units were inoculated with method (1) the spore suspension was pumped into the pump by activation of the pump mechanism, and five units were inoculated with method (2) spore suspension was inoculated on the pump parts before assembling of the pump.

Results: After sterilization the pumps were transferred to TSB medium and incubated for 7 days at 56° C. No growth of bacteria was observed after incubation. By visual inspection no change of materials was detected. By visual inspection no humidity was detected after sterilization.

The above-described pump assembly may be provided in a drug delivery device of the type shown in e.g. EP 1 527 792 or WO 2006/077263, which is hereby incorporated by reference. In a situation of use where the reservoir unit is attached to a transcutaneous device unit the outlet conduit 196 is connected to an inlet of the transcutaneous device unit, and the inlet conduit 195 is connected to a flexible reservoir allowing a fluid to be sucked into the flow path of the pump. The conduits may be pointed or blunt and adapted to be inserted through a corresponding septum or valve.

In the above description of the preferred embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A method comprising the steps of:
providing a device comprising:
a sealed interior portion with at least one opening to the exterior covered by a sterilization barrier formed from a non-porous material allowing a sterilization gas to penetrate but prevents germs from penetrating, wherein:
the device is in the form of a pump with a flow path arranged between an inlet and an outlet, the pump comprising at least one valve member arranged in the flow path, and
the size and configuration of the at least one sterilization barrier formed from a non-porous material comprising liquid silicone rubber allowing at least 50% of the sterilization gas, that would pass between a sterilization gas-containing exterior and the sealed interior portion when a pressure difference is created there between, to pass through the non-porous material,
placing the device in a sterilization enclosure,
creating a relative vacuum in the sealed interior portion by controlling the pressure in the sterilization enclosure,
introducing sterilization gas in the sterilization enclosure thereby raising the pressure therein above the relative vacuum created in the sealed interior portion, and
allowing the sterilization gas to penetrate into the sealed interior portion, whereby at least 50% of the sterilization gas passes between the sterilization enclosure and the sealed interior portion through the at least one sterilization barrier formed from a non-porous material.

2. A method as in claim 1, wherein at least one sterilization barrier formed from non-porous material is moulded in a non-planar configuration.

3. A method as in claim 1, wherein the sterilization gas is steam.

* * * * *

UNITED STATES PATENT AND TRADEMARK OFFICE
CERTIFICATE OF CORRECTION

PATENT NO.        : 8,557,179 B2                        Page 1 of 1
APPLICATION NO.   : 12/740765
DATED             : October 15, 2013
INVENTOR(S)       : Larsen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 676 days.

Signed and Sealed this
Twenty-sixth Day of May, 2015

Michelle K. Lee
*Director of the United States Patent and Trademark Office*